United States Patent [19]

Niemoller

[11] Patent Number: 4,759,720
[45] Date of Patent: Jul. 26, 1988

[54] APPARATUS FOR LEARNING BY THE SUPER-LEARNING METHOD

[75] Inventor: Gerhard Niemoller, Ratekau, Fed. Rep. of Germany

[73] Assignee: Therapy Products Muller oHG, Ratekau, Fed. Rep. of Germany

[21] Appl. No.: 827,259
[22] PCT Filed: Apr. 25, 1985
[86] PCT No.: PCT/DE85/00131
  § 371 Date: Dec. 24, 1985
  § 102(e) Date: Dec. 24, 1985
[87] PCT Pub. No.: WO85/05208
  PCT Pub. Date: Nov. 21, 1985

[30] Foreign Application Priority Data

Apr. 28, 1984 [DE] Fed. Rep. of Germany ....... 3415966

[51] Int. Cl.$^4$ ................................................ G09B 5/04
[52] U.S. Cl. .................................................... 434/319
[58] Field of Search ........................................ 434/319

[56] References Cited

U.S. PATENT DOCUMENTS 3,955,466  5/1976  Goldmark ............................ 434/319
4,354,841  10/1982  Meeder ................................. 434/319

Primary Examiner—Leo P. Picard
Attorney, Agent, or Firm—Balogh, Osann, Kramer, Dvorak, Genova, Genova & Traub

[57] ABSTRACT

The invention relates to an apparatus for learning by the super-learning method, in which the education matter is recorded on a sound tape under adaptation to a preset cadence and expounded to the pupil by playing back the sound tape by means of a sound tape apparatus via an electro-acoustic transducer, for example a pair of headphones. To this end, a piece of music equally recorded on the sound track is played back, at least whilst the educational matter is being listened to for the second time. The educational matter and the music are recorded on and played back from different tracks of a sound tape by means of a multitrack sound tape device, an acoustic speech output and at least one music output of the sound tape apparatus being liable to be mixed in each case. Furthermore, the outputs of the sound tape apparatus and the outputs of one of the following other apparatus components utilized if need be, may be connected to the transducer, namely the output of a cadence generator and/or the output of a biofeedback device for acoustic representation of the prevailing state of relaxation of the pupil.

2 Claims, 1 Drawing Sheet

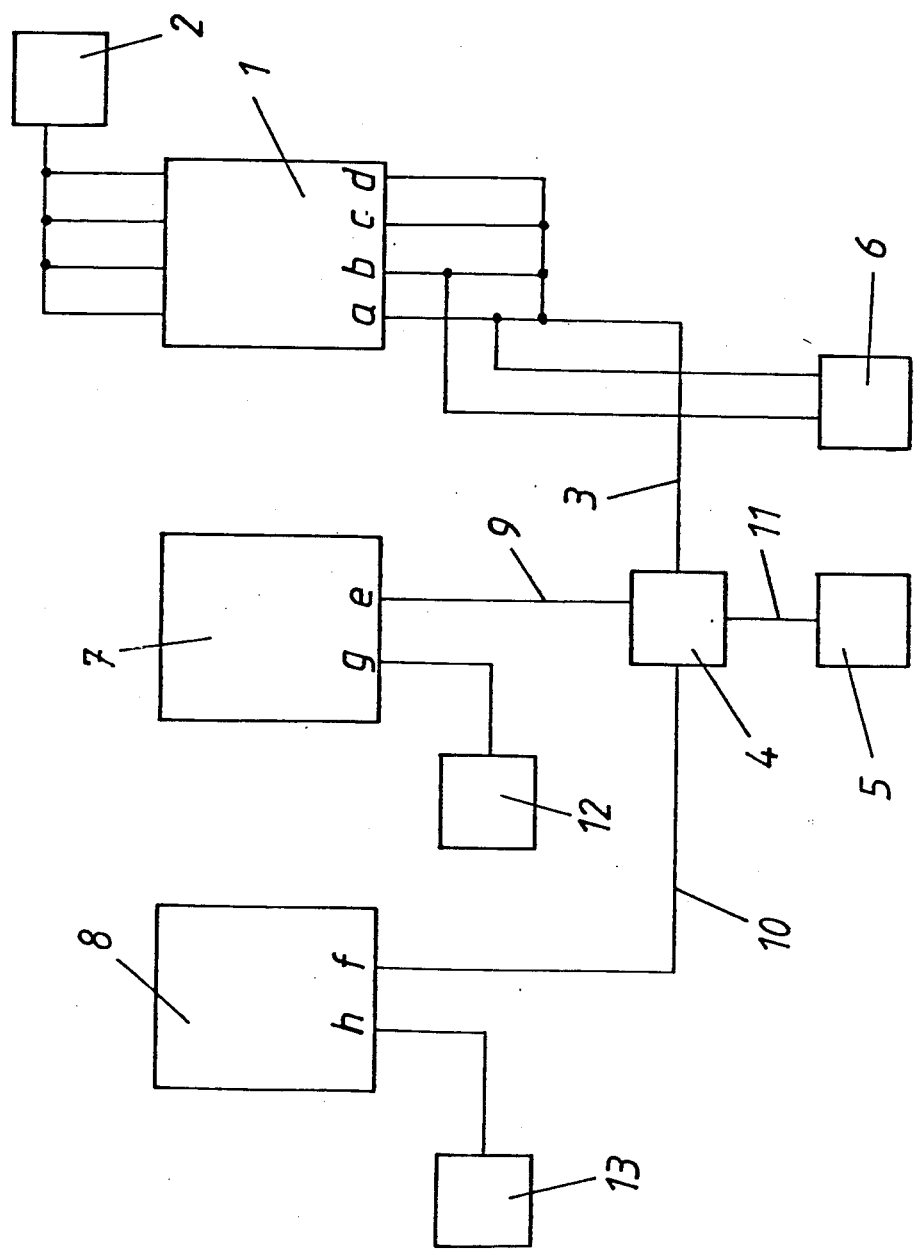

APPARATUS FOR LEARNING BY THE SUPER-LEARNING METHOD

The invention relates to an apparatus for learning by the super-learning method, in which the educational matter is recorded on a sound tape in adaptation to a preset cadence and expounded to the pupil by playing back the sound tape with a sound tape apparatus via an electro-acoustic transducer, being head-phones for preference, at least the second recital of the educational matter being accompanied by a piece of music equally recorded on the sound tape.

The so-called super-learning process is a learning method with which it is possible to increase one's learning performance by a multiple factor by comparison of conventional learning of text, vocabulary and the like. The observation of a series of different conditions is a presupposition for a successful application of this method.

On the one hand, the pupil should be completely relaxed during the learning process, whereas on the other hand, the educational matter has to be recorded on the sound tape in a particular cadence or rhythm and and also played back again in this rhythm during the learning process.

For example, a rhythm of this kind may have a period of 8 s, the educational matter or text passages thereof being recited during 4 s in each case after which an interval of 4 s follows without an educational recital. In this connection, it is equally of importance that the pupil should match his respiratory technique to this rhythm.

Furthermore, it was discovered that optimum learning successes are accomplished if the educational matter is initially simply listened to, and a second subsequent listening action and text recital are accompanied in the background by a piece of super-learning music, which contributes to securing the relaxation and concentration of the pupil. The concentration may finally also be increased by deliberately varying the sound level of the speech recital and with an intonation deviating from the normal idiomatic form.

There are sound tape cassettes on the market on which different languages are already recorded in readiness in this super-learning technique. The possibility also exists however that the educational matter itself may be dictated on to the sound tape. So that the conditions referred to in the foregoing may however be fulfilled to this end, what is commonly still required is a sound tape carrying the recorded clock cadence and another sound tape carrying the super-learning music. It follows from this that at least three sound tape devices or cassette recorders and supplementally a mixing board or desk were required until now, if the separate components needed were to be combined and utilised with each other in a sensible manner.

The object of the invention consists in devising a learning apparatus of lesser complexity in this respect. Furthermore, this apparatus should be simple and reliable to handle and operate.

An apparatus of the kind referred to in the foregoing is taken as a starting point to resolve this problem, and this apparatus is so organised in accordance with the invention that the educational matter and the music may be recorded on and reproduced from different tracks of a sound tape by means of a multitrack sound tape apparatus, that an acoustic speech output and at least one music output of the sound tape apparatus may be mixed in each case and that the outputs of the sound tape apparatus and the outputs of one of the following other apparatus components applicable if required may be connected to the transducer, namely the output of a cadence generator for acoustic representation of the aforesaid cadence and/or the output of a biofeedback device for acoustic representation of the prevailing state of relaxation of the pupil.

An apparatus of this kind consequently is apt to be manageable with a single multitrack sound tape apparatus and with but one sound tape organised to be operated with a plurality of tracks, the recordings on different tracks being liable to be mixed as in the case of conventional sound tape devices. The sound tape apparatus and all other apparatus components may be connected in simple manner to the transducer, separately or in combincation to choice, e.g. by means of a switch.

A control system which automatically and intentionally varies the sound level of the speech recital may complementarily also be connected between the sound tape apparatus and the transducer. Furthermore, the cadence generator and the biofeedback device are appropriately provided with systems for optical representation of the cadence and state of relaxation, so that the pupil may secure orientation acoustically as well as visually.

An example of an embodiment of the invention is illustrated diagrammatically and simplified in the form of a block circuit diagram in the accompanying drawing.

As a sound tape apparatus, use is made for example of a four-track cassette recorder 1 which has a microphone 2 connected to it, so that the educational matter may be recorded on two tracks of the sound tape. The two other tracks are provided for the super-learning music.

The textual educational matter may optionally be picked up at the two outputs a and b of the apparatus 1, and the music from the two other outputs c and d, and channelled via four wires combined into a lead 3 and the switch 4 which is to be set accordingly, to the transducers 5 which is appropriately constructed as headphones. Instead of headphones, it would however also be possible to utilise a loudspeaker, although the latter does not as a rule allow of as satisfactory concentration as does a pair of headphones.

The sound level of the educational matter or speech recital played back may be varied automatically and periodically as required and for the reasons stated in the foregoing, by means of a control system 6 which is connected to the conductors leading to the outputs or terminals a and b and should advantageously be integrated in the apparatus.

The acoustic outputs e and f of the biofeedback device 7 and of the cadence generator 8 may moreover be connected to the headphones 5 via the conductors 9, 10 and 11 by means of the switch 4, whereas other outputs g and h of the components 7 and 8 have systems 12 and 13 connected to them which serve the purpose of providing an optical representation of the signals emitted by these compoents, the acoustic and optical signals containing the same information.

It is possible to operate as follows with the apparatus described. If the tracks provided for the music on the sound tape have not both already been recorded at the works by the makers, this has to be done by the user himself. The education matter is then recorded on an empty track of the sound tape apparatus by means of the microphone 2, that is to say at the rhythm and cadence preset by the cadence generator 7 placed in operation, acoustically via the headphones 5 or optically via the indicator device 12. As already mentioned, it is possible to operate at a rhythm of 8 s to this end, an interval of 4 s in each case following a text of 4 s.

Once the educational matter has been dictated, a relaxation training is begun in preperation for the actual learning process, the state of relaxation established in eah case being depicted by the biofeedback device 7 in visual manner via the indicator system 12, or also in audible manner via the headphones 5 at an appropriate position of the switch 4. Such biofeedback devices are known per se and consequently need not be described in detail. They commonly operate by the principle of measuring the relative skin resistance on the hand or arm of the person in question for example, and of indicating the same, the state of relaxation being the more intensive the lower the skin resistance.

After the pupil has reached an appropriately deep and appropriate state of relaxation, he connects the headphones 5 to the sound tape apparatus 1 by means of the switch 4, and thereby switches said apparatus on in such manner that he first listens to the educational matter without music. In this connection, it is of importance to breathe at the correct rhythm, so that the cadence generator 8 should be switched on for verification, which requires however that the control cadence and the cadence or rhythm of the educational material played back should be set synchronously. Furthermore, the biofeedback device 7 may also be left switched on to check on the prevailing state of relaxation, so that it is possible to detect at any time whether the learning process may perhaps have to be interrupted to perform additional relaxation exercises. As for the rest, it is evident that the multipole switch 4 is so organised that all the specified operating modes may be set by means of the same.

Once the educational matter has been listened to, it is played back again, to which end however the super-learning music is then adjunctively switched together with the text to be learned on the apparatus 1, and is offered to the pupil via the headphones 5, together with the text. The learning process is completed after the text has been listened to twice.

In conclusion, it is also pointed out that the apparatus should appropriately be combined into a compact unit, by housing or installing the apparatus components in question in or on a single casing. The possibility also exists moreover, of mounting the components in question on a carrier or a base plate.

I claim:

1. An apparatus for learning by the super-learning method comprising, a sound tape device containing a multitrack sound tape, the latter containing, or to be provided with, the educational matter being recorded, or to be recorded, on at least one track of said tape in adaptation of a preset cadence, and background music recorded, or to be recorded, onto at least one further track of said tape and multipole switching means for selecting at least one track of said sound tape, an electroacoustic transducer, preferably being headphones, working electrically together with said device through said multipole switching means, wherein said preset cadence and the educational matter being given to the pupil by the transducer, the latter being reproduced by playback of the sound tape by means of said device being actuated by said switching means and wherein at least the second recital of the educational matter being accompanied by background music mixing an acoustic speech output with one music output of said device, further including a cadence generator producing itself acoustic output signals and having an output for acoustic representation of the aforesaid cadence, a biofeedback unit for detecting the prevailing state of relaxation of the pupil by an electrode to be secured to the pupil and having an output for acoustic representation of said prevailing state of relaxation, said cadence generator and said biofeedback unit being directly electrically connected to said switching means for channeling selectively the outputs of said cadence generator and/or of said biofeedback unit to the transducer singly or in combination together with the outputs of said sound tape device, and by a control system which automatically and intentionally varies the sound level of the speed recital and which is connected between the sound tape device and the transducer, whereby the pupil can enhance his learning ability and can himself observe his best state of learning.

2. Apparatus according to claim 1, wherein said biofeedback unit is additionally provided with a system for optical representation of the state of relaxation.

* * * * *